United States Patent [19]

Ueno et al.

[11] Patent Number: 5,549,919
[45] Date of Patent: Aug. 27, 1996

[54] PRESERVATION OF FOODS BY THE COMBINED ACTION OF A NATURAL ANTIMOCROBIAL AGENT AND SEPARATELY PACKAGED DEOXIDIZING AGENT

[75] Inventors: Ryuzo Ueno; Yatsuka Fujita, both of Nishinomiya; Yoshiaki Nagamura, Ushiku; Yuji Kamino, Tsukuba; Akihiko Tabata, Ushiku, all of Japan

[73] Assignee: Kabushiki Kaisha Ueno Seiyaku Oyo Kenkyujo, Osaka, Japan

[21] Appl. No.: 324,375

[22] Filed: Oct. 17, 1994

Related U.S. Application Data

[63] Continuation of Ser. No. 91,478, Jul. 15, 1993, abandoned, which is a continuation of Ser. No. 854,763, Mar. 20, 1992, abandoned, which is a continuation of Ser. No. 460,106, Feb. 9, 1990, abandoned.

[30] Foreign Application Priority Data

Jun. 9, 1988 [JP] Japan .................. 63-144122

[51] Int. Cl.$^6$ ..................... A23B 4/00
[52] U.S. Cl. ............ 426/335; 426/133; 426/326; 426/654
[58] Field of Search ............... 426/335, 424, 426/118, 113, 321, 324, 326, 331, 335, 395, 634

[56] References Cited

U.S. PATENT DOCUMENTS

| | | | |
|---|---|---|---|
| 2,825,651 | 3/1958 | Loo et al. | 426/124 |
| 4,619,995 | 10/1986 | Hayes | 536/20 |
| 4,657,133 | 4/1987 | Komatsu et al. | 426/124 |
| 4,942,048 | 7/1990 | Nasu et al. | 426/271 |
| 4,954,358 | 9/1990 | Ueno et al. | 426/335 |

FOREIGN PATENT DOCUMENTS

| | | |
|---|---|---|
| 0265884 | 5/1988 | European Pat. Off. . |
| 62-186942 | 8/1987 | Japan . |
| 62-143672 | 8/1987 | Japan .................. A23L 3/34 |
| 63-17679 | 1/1988 | Japan .................. A23L 3/34 |

OTHER PUBLICATIONS

Chemical Patent Index, Basic Abstracts Journal Derwent Publications Ltd., London, GB; AN 88-061223 & JP-A-63 017679 (Nichiro Gyogo et al).
Chemical Patent Index, Basic Abstracts Journal Derwent Publications Ltd., London, GB; AN 89-125909 & JP-A-1071439 (Lion Corp).
Patent Abstracts of Japan, vol. 12, No. 76 (C-473) 4 Feb. 1988 (Nippon Kayaku Co. et al) & JP-A-62186942.
Chemical Patent Index, Basic Abstracts Journal Derwent Publications Ltd., GB; AN 84-143209 & JP-A-59074958 (Q.P. Corp).
Chemical Patent Index, Basic Abstracts Journal Derwent Publications Ltd., London, GB; AN 86-241855 & JP-A-61170376 (Seiken KK).
Chemcical Patent Index, Basic Abstracts Journal Derwent Publications Ltd., London, GB; AN 87-217613 & JP-A-62143672 (Inamine S.).

*Primary Examiner*—Leslie Wong
*Attorney, Agent, or Firm*—Sughrue, Mion, Zinn, Macpeak & Seas

[57] ABSTRACT

The present invention relates to the preservation of foods, in which at least one kind of a natural antimicrobial agent selected from the group consisting of protamine, chitosan, and lysozyme to foods is added into the foods, and the foods obtained are stored in the presence of a deoxidizing agent under a substantially sealed condition. According to the present invention, the deterioration of foods by microbes, yeasts and the like which has not been sufficiently prevented by the use of conventional natural antimicrobial agents can be effectively prevented.

8 Claims, No Drawings

PRESERVATION OF FOODS BY THE COMBINED ACTION OF A NATURAL ANTIMOCROBIAL AGENT AND SEPARATELY PACKAGED DEOXIDIZING AGENT

This is a Continuation of application Ser. No. 08/091,478 filed 15 Jul. 1993, now abandoned, which is a continuation of application Ser. No. 07/854,763 filed 20 Mar. 1992, now abandoned, is a Continuation of application Ser. No. 07/460,106, filed as PCT/JP89/00587, Jun. 9, 1989, published as WO89/11801, Dec. 14, 1989, now abandoned.

TECHNICAL FIELD

The present invention relates to a preservation of foods.

BACKGROUND ART

It has been well known that an antimicrobial agent is added to the foods for the preservation. Natural antimicrobial agents such as protamine, chitosan, lysozyme and the like have been used as an antimicrobial agent, but these natural antimicrobial agents are limited in the amount to be added to foods, and are not satisfactorily efficacious in the antimicrobial activity against some kinds of microbe or yeast fungi and so on.

On the other hand, it has been known that the method of controlling oxygen concentration lower by deoxidizing agents or gas substitution is effective to preserve foods, for example, Japanese confections, Western-style cakes, breads, noudles, dry saltery and so forth. These methods are also insufficient to prevent foods from the attack of some kinds of microbe, yeast or fungi and the like. Therefore, the independent preservation methods of foods by use of a natural antimicrobial agent or by the reduction of oxygen gas content using a deoxidizing agent or gas substitution have not led to a satisfactory result because of their insufficient antimicrobial activity against some kinds of microbe, yeast or fungi.

Natural antimicrobial agents, which themselves are used by directly spraying, dipping or mixing into foods are limited in the amount to be used, because they influence delicately the sense of taste and smell if they are used in much amount.

DISCLOSURE OF INVENTION

The object of the present invention is to provide a method of preserving foods, which is broadly effective to prevent foods from deterioration and from denaturation caused by microbe, yeast and/or fungi even in the use of small amount of antimicrobial agents.

The present invention relates to a method of preserving foods which comprises adding at least one kind of a natural antimicrobial agent selected from the group consisting of protamine, chitosan, and lysozyme (this is simply referred to as a natural antimicrobial agent hereinafter) to foods, and storing the food in the presence of deoxidizing agents.

The method of the present invention can be applied to various kinds of foods, for instance, Japanese confections, such as namagashi (soft and fresh Japanese sweets), yokan (sweet jelly of beans), monaka (wafer cake stuffed with bean jam), uirou (rice jelly), habutaemochi (soft rice cake) and the like; Western style cakes such as sponge cake, crepe, pie, fresh cream, custard cream and the like; staple foods such as bread, rice, fresh noodles, rice cake, shiratama (rice-flour dumpling), oshizushi (pressed sushi) and the like; dry salteries or chinmi (gourmet) such as surume (dried squid), niboshi (cooked and dried fish), kunsei (smoking), denbu (tiny bits of fish boiled with sugar and soy sauce), katsuo-bushi (dried bonito), kanpyo (dried gourd shavings), dried shiitake mushroom, dried vegetable, dried fruit and the like; fish or meat processed materials such as kamaboko (boiled fish paste), chikuwa (tube-shaped fish paste), cheese, ham, sausage; an agricultural processed material such as pickles, fruits soaked into sugar, jam and the like; perishable foods such as vegetables, fruits, fish, meats and the like; seasonings such as miso (fermented soybean paste), mentsuyu (soup stock for noodle), liquid seasonings, powder seasonings, furikake (tasty seasoned and dried food for sprinkling over rice), and the like; seasoned foods, sozai (side dish) and the like. A remarkable effect is observed when the method of the present invention is applied to foods of high water content, especially to foods having a water activity more than 0.8, which are difficult to be preserved for a long time by the conventional way.

Examples of a natural antimicrobial agent having an amino group used in the present invention are selected from protamine, chitosan and lysozyme. Co-use of these natural antimicrobial agents gives, of course, a preferable result. Protamine can be used in free state, and mineral acid salts of protamine such as sulfate, chloride and the like may be used. When foods added with any of three kinds of natural antimicrobial agent are stored under sealed condition in the presence of deoxidizing agents, the excellent preservation effect can be achieved.

The natural antimicrobial agent may be used in such an amount that the flavor and tasty of the foods are not spoiled. The amounts are 10–50,000 ppm, preferably 100–2,000 ppm for protamine, 1–10,000 ppm, preferably 5–500 ppm for lysozyme, and 5–50,000 ppm, preferably 10–1,000 ppm for chitosan. These antimicrobial agents may be used singly or mixed.

The natural antimicrobial agent may be added to food materials before cooking, or may be directly added to foods and simply mixed. Alternatively, a solution of the natural antimicrobial agent in suitable solvent such as ethanol or water may be sprayed or sprinkled on foods. And foods can be soaked in the solution.

Foods to which a natural antimicrobial agent was added are sealed together with a deoxidizing agent, and stored in an oxygen free or low oxygen condition, for instance, not more than 0.05%, preferably not more than 0.01%.

As deoxidizing agents, the arbitrary mixture can be used which is made from maily several reducing agents such as sulfites, hydrogensulfites, thiosulfates, dithionites, oxalates, pyrogallol, sodium formaldehydesulfoxylate, glucose, copper-amine complexes, ascorbic acid, iron powders, zinc powders and the like, and supplementarily any other material.

The deoxidizing agent of the present invention may be used in such an amount that the concentration of oxygen in a sealed package can be maintained less than about 0.05%, preferably less than about 0.01%. Generally, it is preferable to use it in excess amount so as to remove oxygen which permeates continuously into the sealed package through a wrapping film with time.

A wrapping material may be anything having the lower oxygen permeability, for example, vinylidenechloride-coated laminate film, a can, a bottle, a jar and the like which can be shut airtightly, though not restrictively.

Any other antimicrobial agent may be used together with the natural antimicrobial agent in the present invention.

The present invention is illustrated by the following Examples.

EXAMPLE 1 and COMPARATIVE EXAMPLE 1

A standard agar plate culture medium (pH 7.0) containing protamine chloride (available from SIGMA, from salmon) in the concentration of 62.5–1,000 ppm was prepared sterilely, onto which a culture solution of microorganisms ($10^6$ cfu/ml) shown in Table 1 was inoculated by a microplanter (MIT-P) available from K. K. Sakuma Seisakusho. The culture medium inoculated was sealed in a bag (volume: 450 cc) of KOP/PE (20μ/50μ) together with a deoxidizing agent Oxylater H-100 (available from Ueno Seiyaku K.K.; iron type deoxidizing agent), and cultured at 30° C. for 2 weeks. The oxygen content in each bag during the test was 0.005–0.009%. The minimum concentration of protamine hydrochloride, at which growth of the microorganisms has been completely inhibited is shown in Table 1.

In the Comparative Example 1 such antimicrobial tests were carried out in the same manner as described in the Example 1 except that no deoxidizing agent was used. The results are shown in Table 1.

In controls which were carried out according to the same manner as in Example 1 except that the protamine chloride was not used, the growth of every microorganisms was observed, though the oxygen concentration was substantially the same as in Example 1.

TABLE 1

| Microorganisms | Example 1 | Comp. Ex. 1 |
|---|---|---|
| L. casei sub sp. rhamnosus IFO 3425 | 250 | 500 |
| L. fermentum IFO 3071 | 250 | 500 |
| L. fructosus IFO 3516 | 250 | 500 |
| L. lactis IFO 3734 | <62.5 | 250 |
| L. murinus IFO 14221 | <62.5 | 500 |
| L. plantarum IFO 3070 | 250 | 500 |
| Leuc. lactis IFO 12455 | 250 | 700 |
| Leuc. mesenteroides IFO 3426 | 250 | 500 |
| Leuc. mesenteroides IAM 1046 | 250 | 500 |
| Streptococcus pyogenes ATCC 19615 | 250 | 700 |
| | | (ppm) |

L.: Lactobacillus,
Leuc.: Leuconostoc

EXAMPLE 2 and COMPARATIVE EXAMPLE 2

A potato dextrose agar plate culture medium (pH 7.0) containing protamine sulfate (available from Wako Junyaku K. K., from herring) at the concentration of 62.5–2,000 ppm was sterilely prepared, onto which yeast culture solution ($10^6$ cfu/ml) was inoculated by a microplanter (MIT-P) available from Sakuma Seisakusho. The culture medium inoculated was sealed in a bag (volume: 450 cc) of KOP/PE (20μ/50μ) together with a deoxidizing agent Oxylater H-100 (available from Ueno Seiyaku K.K.; iron type deoxidizing agent), and cultured at 30° C. for one week. The oxygen content in each bag during the test was 0.005–0.009%. The minimum concentration of protamine sulfate, at which growth of the yeasts has been completely inhibited is shown in Table 2.

In the Comparative Example 2 antimicrobial tests were carried out in the same manner as described in the Example 2 except that no deoxidizing agent was used. The results are shown in Table 2.

In controls which were carried out according to the same manner as in Example 2 except that the protamine sulfate was not used, the growth of every yeast was observed, though the oxygen concentration in each bag was substantially the same as in Example 2.

TABLE 2

| Yeast | Example 2 | Comp. Ex. 2 |
|---|---|---|
| Saccharomyces cerevisiae IAM 4272 | 1,000 | 2,000 |
| Saccharomyces cereviciae IAM 4274 | 1,000 | 2,000 |
| Saccharomyces ovif. Ost. S-73 | 1,000 | 2,000 |
| Candida utilis IFO 0396 | 500 | 1,000 |
| Cryptococcus laurentii IAM 12264 | 500 | 1,000 |
| Rhodotorula rubra IFO 0894 | 500 | 1,000 |
| Rhodotorula rubra IAM 4989 | 250 | 700 |
| Shizosaccharomyces pombe Lindner 0-77 | 700 | 2,000 |
| Torulopsis candida IAM 4976 | 700 | 2,000 |
| Trichosporon cutaneum IAM 12246 | 500 | 1,000 |
| | | (ppm) |

EXAMPLE 3 and COMPARATIVE EXAMPLE 3

A standard agar plate culture medium (pH 7.0) containing lysozyme (available from Seikagaku Kogyo K. K., 6-times crystallized product, from egg white) at the concentration of 1.25–160 ppm was sterilely prepared, onto which a microorganism culture solution ($10^6$ cfu/ml) was inoculated by a microplanter (MIT-P) available from Sakuma Seisakusho. The culture medium inoculated was sealed in a bag (volume: 450 cc) of KOP/PE (20μ/50μ) together with a deoxidizing agent Oxylater H-100 (available from Ueno Seiyaku K.K.; iron type deoxidizing agent), and cultured at 30° C. for one week. The oxygen content in each bag during the test was 0.005–0.009%. The minimum concentration of lysozyme, at which growth of the microorganisms has been completely inhibited is shown in Table 3.

In the Comparative Example 3 antimicrobial tests were carried out in the same manner as described in the Example 3 except that no deoxidizing agent was used. The results are shown in Table 3.

In controls which were carried out according to the same manner as in Example 3 except that the lysozyme was not used, the growth of every microorganisms was observed, though the oxygen concentration was substantially the same as in Example 3.

TABLE 3

| microorganism | Example 3 | Comp. Ex. 3 |
|---|---|---|
| L. casei sub sp. rhamnosus IFO 3425 | 40 | 160 |
| L. plantarum IFO 3070 | 40 | 160 |
| Leuc. lactis IFO 12455 | 40 | 160 |
| Leuc. mesenteroides IFO 3426 | 2.5 | 160 |
| Leuc. mesenteroides IFO 1046 | 40 | 160 |
| | | (ppm) |

L.: Lactobacillus,
Leuc.: Leuconostoc

EXAMPLE 4 and COMPARATIVE EXAMPLE 4

Nutrient Broth (available from Difco, pH 6.0) containing 1% glucose, and chitosan (available from Katayama Kagaku Kogyo K.K.) at a concentration of 7.8–250 ppm was prepared sterilely, onto which each one loop of microorganism culture solution of Table 4 was inoculated. Each culture medium inoculated was sealed in a bag (450 cc) made of KOP/PE (20μ/50μ) together with a deoxidizing agent, Oxylater H-100 (available from Ueno Seiyaku K.K.), cultivated at 30° C. for one week. After that the bag of cultivated medium was opened, one loop of it was inoculated onto a usual agar plate culture medium, and cultivated at 30° C. for 2 days.

The oxygen content in each bag during the test is 0.005–0.009%. The minimum concentration of chitosan, at which growth of the microorganisms has been completely inhibited is shown in Table 4.

In the Comparative Example 4 such antimicrobial tests were carried out in the same manner as described in the Example 4 except that no deoxidizing agent was used. The results are shown in Table 4.

In controls which were carried out according to the same manner as in Example 4 except that the chitosan was not used, the growth of every microorganisms was observed, though the oxygen concentration was substantially the same as in Example 4.

TABLE 4

| microorganisms | Example 4 | Comp. Ex. 4 |
| --- | --- | --- |
| L. casei sub sp. rhamnosus IFO 3425 | <7.8 | 31.3 |
| L. fermentum IFO 3071 | <7.8 | 15.6 |
| L. lactis IFO 3734 | <7.8 | 15.6 |
| L. plantarum IFO 3070 | <7.8 | 31.3 |
| Leuc. lactis IFO 12455 | 15.6 | 31.3 |
| Leuc. mesenteroides IFO 3426 | <7.8 | 62.5 |
| Leuc. mesenteroides IFO 1046 | <7.8 | 31.3 |
| Streptococcus pyogenes ATCC 19615 | <7.8 | 15.6 |
| | | (ppm) |

L.: *Lactobacillus casei* sub sp. rhamnosus,
Leuc.: Leuconostoc

EXAMPLE 5

1. PREPARATION

Hard flour (Midori Naito, Nitto Seifun K. K.) 250 g, salt (purified salt) 8 g, kansui powder (alkaline material obtained by concentrating a lye of a stem of plantain or banana, which is used for increasing the consistency of dough; a reagent) 2.4 g, coloring agent (Rikecolor Y, available from Riken Vitamin K.K.) 0.16 g and aqueous solution containing protamine chloride in a prescribed amount 144 g were mixed by a mixer, and the mixture was pressed by a noodle making machine having a three steps-roller, and then cut by a 10th grade cutter to give nama chukamen (raw chinese noodle).

2. TEST METHOD

Each 50 g of the nama chukamen containing protamine chloride (available from SIGMA, from herring) and one containing no protamine chloride was sealed with the deoxidizing agent (Oxylater H-100, available from Ueno Seiyaku K.K.) and without it in a bag (450 cc) made of KOP/PE (20μ/50μ) respectively, and the preservability of each chukamen at 30° C. was observed.

The preservability was evaluated by observing the occurrence of colony, formation of slime, softening or discoloring of the chukamen, and the like, and expressed by "effective preservable days", which means the number of days during which the above phenomena were not observed.

| Group | Effective Preservable Days |
| --- | --- |
| containing no protamine chloride | 2 |
| containing deoxidizing agent alone | 3 |
| containing protamine chloride 0.1% alone | 2 |
| containing protamine chloride 0.5% alone | 3 |
| containing protamine chloride 0.1% with deoxidizing agent | 5 |

EXAMPLE 6

1. PREPARATION

Churikiko (medium flour; Akanaito, available from Nitto Seifun K.K.) 1 kg was added with 6% aqueous salt (purified) solution containing protamine sulfate in a prescribed amount 350 g, and the mixture was stirred by a Kanto Mixer CS25E Type. The product was extended under pressure, stamped with feet, rolled, and then cut to give nama udon (raw noodle).

2. TEST METHOD

Each 50 g of the nama udon containing protamine sulfate (available from Wako Junyaku K.K., from herring) and one containing no protamine sulfate was sealed with deoxidizing agent (Oxylater H-100, available from Ueno Seiyaku K.K.) and without it in a bag (450 cc) made of KOP/PE (20μ/50μ) respectively, and the preservability of each nama udon at 30° C. was observed.

The preservability was evaluated by observing the occurrence of colony, formation of slime, softening or discoloring of the udon, and the like, and expressed by "effective preservable days", which means the number of days during which the above phenomena were not observed.

3. RESULT

| Group | Effective Preservable Days |
| --- | --- |
| containing no protamine sulfate | 1 |
| containing deoxidizing agent alone | 2 |
| containing protamine sulfate 0.1% alone | 1 |
| containing protamine sulfate 0.5% alone | 1.5 |
| containing protamine sulfate 0.1% with deoxidizing agent | 5 |

EXAMPLE 7

1. PREPARATION

Lighter-colored soy sauce 500 cc, Mirin (Sweet sake for seasoning) 500 cc, soup stock from a dried bonito and a sea tangle 3,000 cc were mixed, boiled for a short time, and then cooled to give soup for buckwheat noodles.

2. TEST METHOD

Each 100 cc of the soup for buckwheat noodles containing with chitosan available from Katayama Kagaku Kogyo K.K. and not containing chitosan was sealed with a deoxidizing agent (Oxylater H-100, available from Ueno Seiyaku K.K.) in a 400 cc of bottle, and the preservability at 30° C. was observed.

Each 1 ml of the soup for buckwheat noodles was used for test of preservability as one test group. The viable count of microorganisms was countered after the cultivation on a standard agar culture medium at 37° C. for 48 hours. The number of mold and yeast was countered after the cultivation on potato dextrose agar culture medium at 30° C. for 3 days. The effective preserving days was defined as the number of days when the viable count of microorganism, mold and yeast increased up to $10^6$/g.

3 RESULTS

| Test Group | effective preserving days |
| --- | --- |
| containing no chitosan | 2 |
| containing deoxidizing agent alone | 3 |
| containing chitosan 100 ppm alone | 3 |
| containing chitosan 250 ppm alone | 5 |
| containing chitosan (100 ppm) with deoxidizing agent | 10 |

THE EFFECT OF THE INVENTION

According to the present invention a remarkable preservative effect can be obtained against the deterioration of foods occurred by yeast or microorganism, which cannot be effectively prevented by a single use of a deoxidizing agent or of a natural antimicrobial agent such as protamine, chitosan, lysozyme and the like. Such a preservation can be effected using the natural antimicrobial agents specified even in the amount of less than half in case of single use thereof.

What is claimed is:

1. A method of preserving food which comprises adding to food at least one kind of natural antimicrobial agent selected from the group consisting of protamine in an amount of from 250–2,000 ppm, chitosan in an amount of from 15.6–1,000 ppm and lysozyme in an amount of from 40–500 ppm, and storing the food in the presence of a deoxidizing agent consisting essentially of iron powders, said deoxidizing agent is packed separately from the food, wherein the food and deoxidizing agent are contained in a sealed package to maintain an oxygen concentration in the sealed package of not more than 0.05%, and the food is preserver from deterioration caused by Lactobacillus, Leuconostoc, Streptococcus, Saccharomyces, Candida, Cryptococcus, Rhodotorula, Shizosaccharomyces, Torulopsis and Trichosporon.

2. The method as claimed in claim 1, wherein the natural antimicrobial agent is protamine.

3. The method as claimed in claim 1, wherein the natural antimicrobial agent is chitosan.

4. The method as in claim 1, wherein the natural antimicrobial agent is lysozyme.

5. The method of preserving food as in claim 1, wherein the oxygen concentration in the sealed package is maintained to less than about 0.01%.

6. The method of preserving food as in claim 1, wherein the sealed package is selected from the group consisting of a can, bottle, jar and film.

7. The method of preserving food as in claim 1, wherein the sealed package is formed from an oxygen impermeable packing and wrapping material.

8. A method of preserving food which comprises adding to food at least one kind of natural antimicrobial agent selected from the group consisting of protamine in an amount of from 250–2,000 ppm, chitosan in an amount of from 15.6–1,000 ppm and lysozyme in an amount of from 40–500 ppm, and storing the food in the presence of a deoxidizing agent consisting essentially of iron powders, said deoxidizing agent is packed separately from the food, wherein the food and deoxidizing agent are contained in a sealed package to maintain an oxygen concentration in the sealed package of not more than 0.05%, and the food is preserved from deterioration caused by a microorganism selected from the group consisting of *Lactobacillus casei, Lactobacillus fermentum, Lactobacillus fructosus, Lactobacillus lactis, Lactobacillus murinus, Lactobacillus plantarum, Leuconostoc lactis, Leuconostoc mesenteroides, Streptococcus pyogenes, Saccharomyces cerevisiae, Saccharomyces ovif. Ost., Candida utilis, Cryptococcus laurentii, Rhodotorula rubra, Shizosaccharomyces pombe Lindner, Torulopsis candida* and *Trichosporon cutaneum*.

* * * * *